US010456374B2

(12) United States Patent
Baldacci

(10) Patent No.: US 10,456,374 B2
(45) Date of Patent: Oct. 29, 2019

(54) PYRROLIDONE CARBOXYLIC ACID (PCA) FOR OPHTHALMIC USE

(71) Applicant: Laboratori Baldacci S.p.A., Pisa (IT)

(72) Inventor: Massimo Baldacci, Pisa (IT)

(73) Assignee: Laboratori Baldacci S.p.A., Pisa (IT)

( * ) Notice: Subject to any disclaimer, the term of this patent is extended or adjusted under 35 U.S.C. 154(b) by 0 days.

(21) Appl. No.: 16/297,398

(22) Filed: Mar. 8, 2019

(65) Prior Publication Data
US 2019/0216778 A1 Jul. 18, 2019

Related U.S. Application Data

(63) Continuation of application No. 15/558,524, filed as application No. PCT/IB2016/051934 on Apr. 6, 2016, now Pat. No. 10,272,067.

(30) Foreign Application Priority Data

Apr. 9, 2015 (IT) .................. 102015000011216

(51) Int. Cl.
| | | |
|---|---|---|
| *A61K 31/4015* | (2006.01) | |
| *A61K 31/728* | (2006.01) | |
| *A61K 9/00* | (2006.01) | |
| *A61K 33/34* | (2006.01) | |

(52) U.S. Cl.
CPC ........ *A61K 31/4015* (2013.01); *A61K 9/0048* (2013.01); *A61K 31/728* (2013.01); *A61K 33/34* (2013.01)

(58) Field of Classification Search
None
See application file for complete search history.

(56) References Cited

U.S. PATENT DOCUMENTS

| | | | |
|---|---|---|---|
| 2007/0297981 A1 | 12/2007 | Ousler, III et al. | |
| 2013/0064911 A1 | 3/2013 | Yoshpe et al. | |
| 2014/0171490 A1 | 6/2014 | Gross et al. | |
| 2014/0242176 A1* | 8/2014 | Robledo | A61K 31/7048 424/490 |
| 2017/0224766 A1* | 8/2017 | Lim | A61K 38/13 |

FOREIGN PATENT DOCUMENTS

| | | |
|---|---|---|
| GB | 2456528 A | 7/2009 |
| WO | 2007/061200 A1 | 5/2007 |
| WO | 2012/092375 A1 | 7/2012 |

OTHER PUBLICATIONS

Barel, et al., Handbook of Cosmetic Science and Technology, Third Edition, pp. 357-370, 2009.
Ghate, et al., "Barriers to Glaucoma Drug Delivery", J Glaucoma, vol. 17, No. 2, Mar. 2008, pp. 147-156.
Pescina, et al., "Development of a Convenient ex vivo Model for the Study of the Transcomeal Permeation of Drugs: Histological and Permeability Evaluation", Journal of pharmaceutical sciences, vol. 104; Published online Nov. 12, 2014 in Wiley Online Library (wileyonlinelibrary.com), pp. 63-71.
Saettone, et al., "Evaluation of ocular permeation enhancers: In vitro effects on corneal transport of four β-blockers, and in vitro/in vivo toxic activity", International Journal of Pharmaceutics, vol. 142, Issue 1, Sep. 27, 1996, pp. 103-113.
Shirasaki, "Molecular Design for Enhancement of Ocular Penetration", Journal of Pharmaceutical Sciences, vol. 97, No. 7, Jul. 2008; Published online in Wiley InterScience (www.interscience.wiley.com), pp. 2462-2496.
Smith, et al., "Percutaneous Penetration Enhancers", CRC Press, 1995, pp. 214-215.
Stahl, et al., "Handbook of Pharmaceutical Salts : Properties, Selection, and Use", International Union of Pure and Applied Chemistry (IUPAC), Wiley-VCH, 2008, pp. 127-133.
Wilhelmus, "The Draize Eye Test", Survey of Ophthalmology, vol. 45 No. 6, May-Jun. 2001, pp. 493-515.
International Search Report dated Aug. 17, 2016 in International Application No. PCT/IB2016/051934.
Aragona, P. et al., "Sodium hyaluronate eye drops of different osmolarity for the treatment of dry eye in Sjögren's syndrome patients", British Journal of Ophthalmology, vol. 86, No. 8, Aug. 1, 2002, pp. 879-884.
Yao, K. et al., "Efficacy of 1% carboxymethylcellulose sodium for treating dry eye after phacoemulsification: results from a multi-center, open-label, randomized, controlled study", BMC Ophthalmology. vol. 15, No. 1, Mar. 20, 2015, 10 pages.

* cited by examiner

*Primary Examiner* — Nannette Holloman
(74) *Attorney, Agent, or Firm* — Perkins Coie LLP; Viola T. Kung

(57) ABSTRACT

The present invention relates to pyrrolidone carboxylic acid (PCA) and/or pharmaceutically acceptable salts or derivatives thereof for use in the treatment of ocular diseases and/or disorders.

A further object of the present invention are compositions comprising pyrrolidone carboxylic acid (PCA) and/or pharmaceutically acceptable salts or derivatives thereof, at least one physiologically acceptable excipient, and optionally at least one additional active ingredient for use in the treatment of ocular diseases and/or disorders.

10 Claims, 1 Drawing Sheet

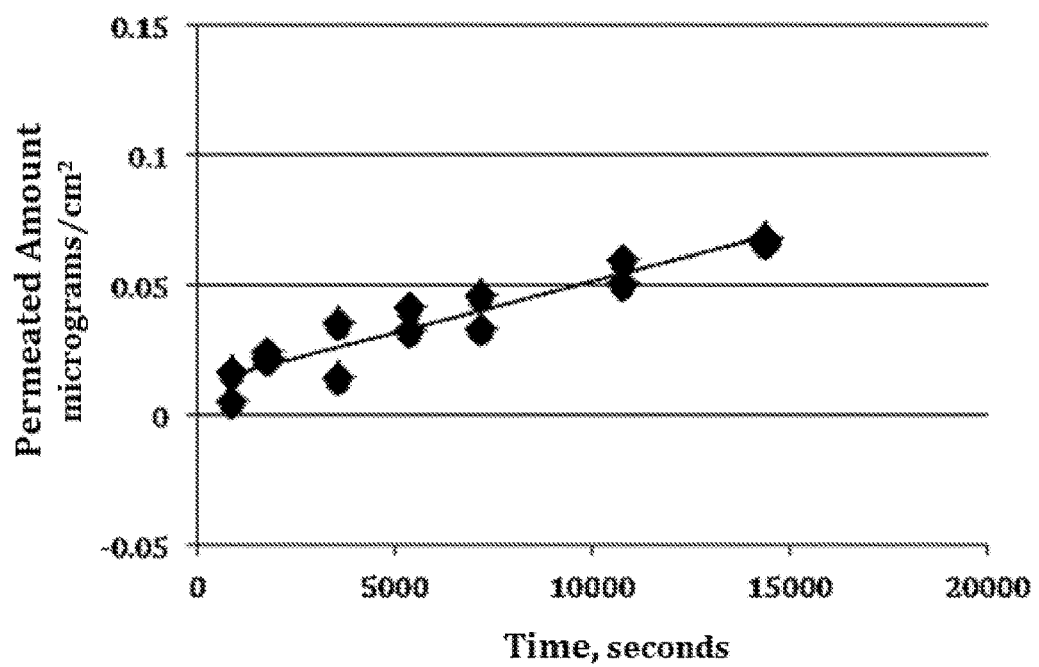

PYRROLIDONE CARBOXYLIC ACID (PCA) FOR OPHTHALMIC USE

This application is a continuation of U.S. application Ser. No. 15/558,524, filed Sep. 14, 2017; which is National Stage of International Application PCT/IB2016/051934, filed Apr. 6, 2016, published Oct. 13, 2016, under PCT Article 21(2) in English; which claims the priority of Italian Application No. 102015000011216, filed Apr. 9, 2015. The contents of the above-identified applications are incorporated herein by reference in their entireties.

DESCRIPTION

The object of the present invention is pyrrolidone carboxylic acid (PCA) and/or pharmaceutically acceptable salts or derivatives thereof for use in the treatment of ocular diseases and/or disorders.

A further object of the present invention are compositions comprising pyrrolidone carboxylic acid (PCA) and/or pharmaceutically acceptable salts or derivatives thereof, at least one physiologically acceptable excipient, and optionally at least one additional active ingredient for use in the treatment of ocular diseases and/or disorders

STATE OF THE ART

Disease and/or disorders of the eye may occur at any age, starting from pediatric age. Dry eye disease is a disorder that results from poor tear production (lacrimal hyposecretion): due to a partial or complete atrophy, or to alterations often of hormonal basis the glands do not longer produce sufficient tear fluid, and the eye becomes therefore more or less dry.

Sometimes, the drainage system is too active.

All this results in a greater traumatism due to continuous movement of the eyelids on the ocular surface with each blinking, and an insufficient cleaning of the same from foreign bodies or germs. In addition, there is a lack of antibodies and lysozyme, tear components with high bactericidal power: the risk of contracting infections is therefore very high, even with commonly harmless germs. The most common symptoms of dry eye disease are burning, foreign body sensation in the eye, photophobia, difficulty in opening the eyelids on awakening and, in severe cases, pain and blurred vision. All these disorders increase in dry, windy environments, or where heating and air conditioning are in function. Sometimes, patients suffering from lacrimal hyposecretion have profusely watering eyes (especially in the presence of keratitis, a damage to the corneal surface): the tear fluid is however very watery, contains few mucous components, and evaporates quickly leaving the cornea exposed to the action of external agents. Many people with dry eye disease also suffer from disorders of the throat and the paranasal sinus, such as nasal congestion or sinusitis, chronic cough, frequent colds, seasonal allergies, congestion in the ear center, headaches.

Generally, two forms of dry eye disease are distinguished:
primary (Sjögren Syndrome), i.e. ocular manifestation of a general autoimmune disease, such as, for example, lupus erythematosus, rheumatoid arthritis, scleroderma;
secondary, due to excessive evaporation of the tear film (blepharitis, conjunctivitis, prolonged use of contact lenses, senile reduced secretion, reduced secretion due to medications, hypovitaminosis A, prolonged use of eye drops).

Dry eye disease is the most common ocular pathology in the world; 11% of people aged between 30 and 60 years, and 14% of people older than 65 years suffer from this disorder or disease.

Dry eye disease (also called "dry eye") can lead to serious vision disturbances and tear film instability, with possible serious damage to the ocular surface.

In most cases, dry eye involves hyperosmolarity of the tear film, and inflammation of the ocular surface.

The key pathogenetic mechanisms of dry eye are: reduced tear production and/or excessive evaporation, hyperosmolarity, inflammation with damage to the epithelial cells, and tear film instability (cornea-tears interface).

In such a situation, a transitory profile (i.e. envisaging a recovery) may be generated or, when the pathological profile persists over time, with continuing cell damage without treatment, the disease becomes irreversible.

To date, there is no definitive treatment for dry eye disease or its related disorders (hyperosmolarity or inflammation). Despite the availability of many topical therapeutic aids (tear substitutes), the long-term results of tear film diseases therapy are often discouraging and not very durable.

The use of a tear substitute has to maintain a good visual acuity in the patient and restore comfort.

Normally, the lacrimal pH is around 7.2-7.4. The patients report a well-being feeling with alkaline eye drops. Normally, artificial tears are pH buffered. The frequency of the number of the drops in the day may vary depending on the disease phase and the tear substitute used; sometimes, in the acute phases, the instillation of tear substitutes is required every hour, while, at best of times, it can be up to 5-6 times a day. Nevertheless, for the patient it is critical to maintain always a well hydrated eye and, in most cases, this requires the instillation of the tear substitute every hour, or at least every 2-3 hours. Clearly, the large number of repeated instillations doesn't make the treatment easy and pleasing to the patient, and generates discomfort.

There is a solution offered by contact lenses, often attempted when the tear substitutes do not offer any advantage. However, the use of contact lenses is often not really feasible as, in the event of lacrimal hyposecretion, with marked reduction of the aqueous component, the contact lenses are not tolerated by the patient.

There is the surgical solution, which in some cases may help the ocular surface regeneration. The simplest and most widely used surgical therapy in the treatment of dry eye diseases is to close, temporarily or permanently, the lower and/or upper tear punctum by means of small silicon caps ("punctum plugs"). It is, however, apparent that the surgical solution entails drawbacks and discomfort to the patient.

Inflammation or infection of the cornea, also called keratitis, may be of viral (for example adenoviruses, herpesviruses), bacterial or fungal origin. The cornea is a transparent membrane located on the front of the eye, therefore particularly exposed to the outside. This type of inflammations or infections may progress until appearance of erosions or ulcers of the cornea, which alter the visual acuity and make it cloudy. To date, the most common treatment is the administration of antibacterial or antiviral drops. In case of keratitis of herpetic origin, the treatment with antiviral agents is often indispensable.

Very often inflammations or infections of bacterial, viral or fungal origin occur when the eye is already subject to dryness itself. In case of dry eye, in fact, the onset of inflammatory or infective phenomena of various origin is very frequent, whose treatment is made more complex and difficult.

It is therefore still felt the need for an effective treatment of the diseases and/or disorders of the eye, in particular one able to ensure an improved hydration long lasting over time. In addition, it is still felt the need for an effective treatment to fight infections and/or inflammations of various origin, which are very often established at ocular level, especially in case of ocular dryness.

Pyrrolidone carboxylic acid (PCA), shown in the formula below, is a cyclic organic compound, also known as pyroglutamic acid.

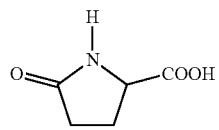

In the literature, the action of PCA as a vector to promote an improved gastrointestinal adsorption of drugs has long been described (Barel et al. Handbook of Cosmetic Science and Technology, Third Edition, pages 357-370, 2009; Smith et al. Percutaneous Penetration Enhancers, CRC Press, pages 214, 1995). The emollient and moisturizing properties of the product are also known, when it is used in various cosmetic compositions for skin and hair care.

PCA is added in the European databank of Cosmetic Ingredients as a humectant and moisturizer: ec.Europa.eu/consumers/cosmetics/cosing.

No toxic and/or harmful effects have ever been found, neither when this compound has been used topically nor when administered, even in high doses, in humans and laboratory animals.

Definitions

Unless otherwise defined, all terms of the art, notations and other scientific terms used herein are intended to have the meanings commonly understood by those skilled in the art to which this description belongs. In some cases, terms with meanings that are commonly understood are defined herein for clarity and/or ready reference; therefore, the inclusion of such definitions herein should not be interpreted as being representative of a substantial difference with respect to what is generally understood in the art.

The term "pharmaceutically acceptable salts or derivatives" refers to those salts or derivatives which possess the biological effectiveness and properties of the salified or derivatized compound, and that do not produce adverse reactions when administered to a mammal, preferably a human being. The pharmaceutically acceptable salts may be inorganic or organic salts; examples of pharmaceutically acceptable salts include, but are not limited to: carbonate, hydrochloride, hydrobromide, sulfate, hydrogen sulfate, citrate, maleate, fumarate, trifluoroacetate, 2-naphthalenesulfonate, and para-toluenesulfonate. Additional information on pharmaceutically acceptable salts may be found in Handbook of pharmaceutical salts, P. Stahl, C. Wermuth, WILEY-VCH, 127-133, 2008, incorporated herein by reference. The pharmaceutically acceptable derivatives include esters, ethers and N-oxides.

The term "physiologically acceptable excipient" refers to a substance devoid of any pharmacological effect of its own, and that does not produce adverse reactions when administered to a mammal, preferably a human being. Physiologically acceptable excipients are well known in the art and are described, for example, in Handbook of Pharmaceutical Excipients, sixth edition 2009, incorporated herein by reference.

The term "simultaneous, separate or sequential use" refers to the simultaneous administration of the first and the second compound, or in such a way that the two compounds will act on the eye of the patient at the same time, or to the administration of a compound after the other compound in such a way to provide a therapeutic effect. In some embodiments, a compound is administered to a patient for a period of time, followed by the administration of the other compound.

The terms "comprising", "having", "including" and "containing" are to be intended as open terms (i.e., meaning "comprising, but not limited to"), and are to be considered as a support also for terms such as "consist essentially of", "consisting essentially of", or "consisting of".

The term "pediatric age" refers to the population aged 0-18 years.

The term "q.s." refers to the amount needed to reach the indicated target volume.

DESCRIPTION OF THE DRAWINGS

FIG. 1—Permeation profile of pyrrolidone carboxylic acid (PCA) through isolated rabbit cornea, following the experiment performed in Example 9.

DESCRIPTION OF THE INVENTION

It has now surprisingly been found that pyrrolidone carboxylic acid is especially effective for use in the treatment of ocular diseases and/or disorders.

An object of the present invention is therefore pyrrolidone carboxylic acid and/or salts or pharmaceutically acceptable derivatives thereof for use in the treatment of ocular diseases and/or disorders.

An object of the present invention is also pyrrolidone carboxylic acid and/or salts or pharmaceutically acceptable derivatives thereof, in combination with at least one additional active ingredient for simultaneous, separate or sequential use in the treatment of ocular diseases and/or disorders.

A further object of the present invention is a pharmaceutical formulation comprising pyrrolidone carboxylic acid and/or salts or pharmaceutically acceptable derivatives thereof, and at least one physiologically acceptable excipient for use in the treatment of ocular diseases or disorders.

Still a further object of the present invention is a pharmaceutical formulation comprising pyrrolidone carboxylic acid and/or salts or pharmaceutically acceptable derivatives thereof, and at least one additional active ingredient, and at least one physiologically acceptable excipient for use in the treatment of ocular diseases and/or disorders.

According to a preferred aspect of the invention, said ocular diseases and/or disorders are selected from ocular dryness (dry eye disease, also called "dry eye"), ocular hyperosmolarity, ocular inflammations and/or ocular infections.

According to a more preferred aspect of the invention, said ocular disease and/or disorder is ocular dryness. The ocular dryness according to the present invention can be primary or secondary.

Very frequently, the ocular dryness is generated by or generates hyperosmolarity, resulting in a worsening of the dry eye profile, eventually evolving into an irreversible disease.

According to a preferred aspect of the invention, said hyperosmolarity may be due to dry eye or may be primary and generate dryness of the eye.

According to another preferred aspect of the invention, said ocular inflammations and/or infections are inflammations and/or infections of the cornea (keratitis), and may be of bacterial, viral or fungal origin. When said keratitises are of viral origin, they are for the most part due to adenovirus or herpes virus.

Very frequently, such inflammations and/or infections of the cornea occur in the eye already characterized by dryness; it then becomes more and more complex to act effectively on it.

According to an aspect of the invention, said at least one additional active ingredient may be selected from a metal salt, hyaluronic acid, a cellulose derivative, polyacrylate, an osmoprotectant, polysaccharides and derivatives thereof.

According to another aspect of the invention, said metal salt is selected from a copper, zinc, sodium, or manganese salt, or a mixture thereof.

According to another aspect of the invention, said metal salt is selected from sulfate, phosphate, or a mixture thereof. According to a preferred aspect, said metal salt is copper sulfate.

According to a further aspect of the invention, said osmoprotectant is selected from erythritol, taurine, L-carnitine, or a mixture thereof.

According to yet a further aspect of the invention, said cellulose derivative is selected from carboxymethyl cellulose, ethyl cellulose, hydroxypropyl cellulose, or a mixture thereof.

According to an aspect of the invention, said at least one physiologically acceptable excipient is selected from preservatives, antioxidants, buffering agents, moisturizers, stabilizers, surfactants, aqueous vehicles, oleaginous vehicles, humectants, gelling agents, or mixtures thereof. According to a preferred aspect, said at least one excipient is a buffering system and/or a preservative.

According to an aspect of the invention, the pharmaceutical formulation of the invention is in a liquid or semi-solid form. According to a preferred aspect, the formulation of the invention is in the form of a solution (more preferably an aqueous solution), suspension, cream, ointment, gel, or spray. The gel formulation of the invention may be in the form of a droppable gel, i.e. a gel that may be applied dropwise (not in a semi-solid vehicle). Furthermore, the formulation may be a solution to be administered preferably in the form of a spray, in particular in forms of blepharitis due to dryness.

According to an aspect of the invention, the pharmaceutical formulation of the invention is administered in the form of collyrium, eye drops, artificial tears or droppable gel, and may in each case be in a single-dose or multi-dose form; more preferably in a single-dose form.

According to a preferred aspect, the pharmaceutical formulation of the invention is in the form of single-dose collyrium, single-dose eye drops, or single-dose droppable gel.

According to an aspect of the invention, the pharmaceutical formulation has a pH between 6 and 7.5, preferably between 6.6 and 7, so as to be physiologically applicable to the eye, without generating any undesirable effect. Similarly, the pharmaceutical formulation has optimal characteristics of chemical and physical stability; the formation of precipitates on the bottom is not observed, even after days of storage at 4° C. (for example, in a refrigerator). Said pH is obtained by the addition of suitable buffers, such as, for example, phosphate buffer.

According to a preferred aspect, pyrrolidone carboxylic acid (PCA) and/or pharmaceutically acceptable salts or derivatives thereof, is contained in the pharmaceutical formulation of the invention in an amount comprised between 0.05% and 1%, based on the total weight of the formulation, more preferably in an amount of about 0.1-0.2% by weight.

According to a preferred aspect, said at least one additional active ingredient is contained in the pharmaceutical formulation of the invention in an amount comprised between 0.0005% and 0.2% by weight, based on the total weight of the formulation, more preferably in an amount of about 0.001-0.002%, when said active ingredient is a metal salt; when it is, instead, hyaluronic acid or other active ingredients, it is contained in the formulation in an amount comprised between 0.05 and 1%, preferably in an amount of about 0.1-0.2%.

According to a further preferred aspect, the present invention is directed to the use in the treatment of ocular diseases and/or disorders in humans, intended both as adult and in pediatric age.

Pyrrolidone carboxylic acid (PCA) of the invention showed a surprising effect in improving and maximizing hydration of the eye, especially in terms of duration of the hydration and effect on water retention inside the eye tissue.

Pyrrolidone carboxylic acid (PCA) remains in fact at the level of the ocular tissue for a much longer period of time than the compounds currently used in the treatment of ocular dryness. PCA remains in the ocular tissue for a period of time greater than 3 hours, when normally a product indicated for the treatment of ocular dryness remains there for no longer than 1 hour.

It is therefore apparent that a formulation containing pyrrolidone carboxylic acid (PCA) may be applied to the eye that requires hydration for a number of times significantly lower, compared to formulations presently known. Indicatively, in case of ocular dryness, the known products are applied from 6 to 8 times a day, while a formulation containing PCA according to the present invention would be applied from 1 to 3 times a day, improving the compliance of the patient or subject concerned.

In the case of ocular dryness, the reduction in the repetition of the administration is of great importance in order to improve the treatment, and the impact thereof in the life of the subject or patient. A result of the improved hydration is also the refreshing power that the formulation provides when administered.

The combination of at least one additional active ingredient with PCA generated a synergistic effect in the ocular treatment of the invention.

In particular, addition of copper sulfate to PCA surprisingly resulted in a synergistic effect in the ocular treatment, especially in the case of inflammations and/or infections of the cornea (keratitis) of bacterial or viral origin. Thanks to the combination of PCA and copper sulfate, it has been possible to maximize the antibacterial and/or antiviral effect of the two active ingredients, with reduction in the value of the minimum inhibitory concentration for the pathogen generating inflammations and/or infection of approximately eight times.

The combination of PCA and copper sulfate is particularly advantageous because it is able to intervene and act at the level of the conjunctival sac, where the attack of bacteria and/or viruses from the external environment is particularly burdensome.

The addition of at least one osmoprotectant has instead surprisingly generated a synergistic effect with PCA in restoring the cellular volume, by making the eye tissue able to retain greater amounts of water, resulting in improved stabilization of cell functions and blocking the hyperosmolarity that is very often generated in case of dry eye.

The addition of hyaluronic acid has instead surprisingly generated a synergy in terms of moisturizing effect. The hyaluronic acid is, in fact, a coadhesive and binds to the corneal surface holding PCA, which exerts the humectant and moisturizing effect, prolonging even more the moisturizing effect of PCA.

A further advantage provided by pyrrolidone carboxylic acid, as well as by its combination with additional active ingredients, is its power to refresh the ocular tissue, in particular in the case of ocular dryness and/or hyperosmolarity.

The following examples are intended to better illustrate the present invention without limiting it in any way.

Example 1

| Single-dose eye drops | g/100 ml |
| --- | --- |
| Pyrrolidone carboxylic acid (PCA) | 0.10 g |
| Chamomile distilled water | 10.00 g |
| Dibasic sodium phosphate dodecahydrate | 0.60 g |
| Monobasic sodium phosphate monohydrate | 0.06 g |
| Sodium chloride | 0.70 g |
| Edetate disodium dihydrate | 0.05 g |
| Water q.s. | 100 ml |

The formulation is clear, colorless.
There are no precipitates or sediments on the bottom, even after a few days storage in the refrigerator.
pH=6.60
Osmolality (mOsmol/Kg)=298

Example 2

| Single-dose eye drops | g/100 ml |
| --- | --- |
| Pyrrolidone carboxylic acid (PCA) | 0.10 g |
| Hyaluronic acid | 0.20 g |
| Monobasic sodium phosphate monohydrate | 0.06 g |
| Dibasic sodium phosphate dodecahydrate | 0.60 g |
| Sodium chloride | 0.70 g |
| Water q.s. | 100 ml |

The formulation is clear, colorless.
There are no precipitates or sediments on the bottom, even after a few days storage in the refrigerator.
pH=6.60
Osmolality (mOsmol/Kg)=289

Example 3

| Ophthalmic gel | g/100 ml |
| --- | --- |
| Pyrrolidone carboxylic acid (PCA) | 0.1000 g |
| Copper sulfate | 0.0001 g |
| Carbopol 980 | 0.2000 g |
| Lemongrass (citronella essential oil) | 0.025 g |
| EDTA | 0.0100 g |
| 20% Sodium hydroxide | 0.4200 g |
| Sorbitol | 4.0000 g |
| Water q.s. | 100 ml |

This preparation is a droppable gel. There are no precipitates or sediments on the bottom, even after a few days storage in the refrigerator.
pH=6.13
Osmolality (mOsmol/Kg)=248

Example 4

| Multi-dose eye drops | g/100 ml |
| --- | --- |
| Pyrrolidone carboxylic acid (PCA) | 0.1 |
| Copper sulfate | 0.0001 |
| *Hamamelis* distilled water | 10.000 g |
| *Euphrasia* distilled water | 10.000 g |
| Chamomile distilled water | 10.000 g |
| Cornflower distilled water | 10.000 g |
| Dibasic sodium phosphate dodecahydrate | 0.30 g |
| Monobasic sodium phosphate monohydrate | 0.03 g |
| Sodium chloride | 0.80 g |
| Edetate disodium dihydrate | 0.050 g |
| Benzalkonium chloride | 0.01 g |
| Water q.s. | 100 ml |

Example 5

| Single-dose eye drops | g/100 ml |
| --- | --- |
| Pyrrolidone carboxylic acid (PCA) | 0.05 |
| Copper sulfate | 0.0001 |
| Hyaluronic acid | 0.2 g |
| Monobasic sodium phosphate monohydrate | 0.01 g |
| Dibasic sodium phosphate dodecahydrate | 0.10 g |
| Sodium chloride | 0.6 g |
| Benzalkonium chloride EP | 0.01 g |
| Edetate disodium dihydrate | 0.05 g |
| Water q.s. | 100 ml |

Example 6

| Single-dose eye drops | g/100 ml |
| --- | --- |
| Pyrrolidone carboxylic acid (PCA) | 0.05 |
| Copper sulfate | 0.0001 |
| Hyaluronic acid | 0.2 g |
| Monobasic sodium phosphate monohydrate | 0.01 g |
| Dibasic sodium phosphate dodecahydrate | 0.10 g |
| Sodium chloride | 0.80 g |
| Water q.s. | 100 ml |

Example 7

| Multi-dose eye drops | g/100 ml |
| --- | --- |
| Pyrrolidone carboxylic acid (PCA) | 0.1 |
| Copper sulfate | 0.0001 |

-continued

| Multi-dose eye drops | g/100 ml |
|---|---|
| Sodium carboxymethyl cellulose (Caramellose sodium) | 3.50 g |
| Sodium chloride | 0.80 g |
| Benzalkonium chloride | 0.010 g |
| Water q.s. | 100 ml |

Example 8

| Ophthalmic gel | g/100 ml |
|---|---|
| Pyrrolidone carboxylic acid (PCA) | 0.1 |
| Copper sulfate | 0.0001 |
| Hyaluronic acid | 0.40 g |
| Hydroxyethyl cellulose | 1.00 g |
| Tromethamine | 0.20 g |
| Lemongrass (citronella essential oil) | 0.025 g |
| Boric acid | 0.40 g |
| Cetrimide | 0.01 g |
| Sodium edetate | 0.05 |
| Water q.s. | 100 ml |

Example 9

Evaluation of the Biocompatibility of the Formulations of Examples 1, 2 and 4 by Means of Eye Irritation Test (Draize Test)

The eye-irritation test aims to assess any irritation that the formulations of Examples 1, 2 and 4 may cause when administered in vivo. The lack of eye irritation is an indication of the biocompatibility of the formulations and their potential therapeutic efficacy. In fact, after administration, the formulations of Examples 1, 2 and 4 will remain in contact with the ocular surface for a time sufficient to promote the therapeutic activity, and their elimination will be subject only to the normal physiological processes of the precorneal area. Conversely, the appearance of irritative effects, however slight, would negate the possibility for the pyrrolidone carboxylic acid (PCA), conveyed in the formulations of Examples 1, 2 and 4, to remain in contact with the ocular surface for a time sufficient to promote the therapeutic activity. The appearance of irritative effects would promote, in fact, the activation of physiological systems of protection in the eye (increased lacrimation, increase in not productive absorption, increased elimination rate from the precorneal area), resulting in a drastic reduction in the bioavailability.

EXPERIMENTAL DESIGN

Examined preparations (composition) and treatment schedule:
Experimental Solutions:
Solution 1 (Formulation of Example 1):
  Pyrrolidone carboxylic acid (PCA) 0.10 g/100 mL;
  Chamomile distilled water 10.0 g/100 mL;
  Monobasic sodium phosphate monohydrate 0.06 g/100 mL;
  Dibasic sodium phosphate dodecahydrate 0.60 g/100 mL;
  Edetate disodium dihydrate 0.05 g/100 mL;
  Sodium chloride 0.7 g/100 mL.
Solution 2 (Formulation of Example 2):
  Pyrrolidone carboxylic acid (PCA) 0.10 g/100 mL;
  Hyaluronic acid 0.20 g/100 mL;
  Monobasic sodium phosphate monohydrate 0.06 g/100 mL;
  Dibasic sodium phosphate dodecahydrate 0.60 g/100 mL;
  Sodium chloride 0.70 g/100 mL.
Solution 3 (Formulation of Example 4):
  Pyrrolidone carboxylic acid (PCA) 0.10 g/100 mL;
  Copper sulfate 0.0001 g/100 mL;
  Hamamelis distilled water 10.0 g/100 mL;
  Euphrasia distilled water 10.0 g/100 mL;
  Chamomile distilled water 10.0 g/100 mL;
  Cornflower distilled water 10.0 g/100 mL;
  Monobasic sodium phosphate monohydrate 0.03 g/100 mL;
  Dibasic sodium phosphate dodecahydrate 0.30 g/100 mL;
  Sodium chloride 0.80 g/100 mL;
  Edetate disodium dihydrate 0.05 g/100 mL;
  Benzalkonium chloride 0.01 g/100 mL
Reference Solutions The reference solutions had a composition correspondent to the experimental solutions (Sol 1-Sol 3) but devoid of the active ingredients, i.e. Pyrrolidone carboxylic acid (Reference 1), Pyrrolidone carboxylic acid and Hyaluronic acid (Reference 2), Pyrrolidone carboxylic acid and copper sulfate (Reference 3).

TABLE 1

In vivo treatment schedule

| Eye | Preparation | Treatment volume/dose |
|---|---|---|
| Right (OD) | Experimental solution 1 (group 1) | 10 µl |
| Right (OD) | Experimental solution 2 (group 2) | 10 µl |
| Right (OD) | Experimental solution 3 (group 3) | 10 µl |
| Left (OS) | Reference solution 1 (group 1) | 10 µl |
| Left (OS) | Reference solution 2 (group 2) | 10 µl |
| Left (OS) | Reference solution 3 (gruppo 3) | 10 µl |

Animal Species

New Zealand albino rabbits. The "New Zealand" albino rabbit was chosen since it is recognized as an appropriate experimental model for evaluating ocular irritation. Rabbits are often preferred over other animals since their eye is a well-known organ in terms of anatomy and physiology, as well as for its large size. In addition, the eyes of rabbits are generally more susceptible to irritating substances than the eyes of humans. The number of animals to be treated depends on the objectives to be achieved, it has however always to be considered that the fewest animals possible are to be exposed to toxic substances; generally, between 3 and 6 animals are used.

Administration Route

The ocular administration is the expected one for humans.

Number of Animals and Provenance 18 male New Zealand albino rabbits, Pampaloni Fauglia (PI), randomly divided into 6 groups of three units each.

Pharmacological Treatment

A volume of 100 µl was used by Friedenwald and Draize (Wilhelmus, 2001; Survey Ophthalmology, 45:493-515) and had been chosen as this amount was commonly used for instillation or injection in the eye. Later researches have shown that a volume of 10 µl or lower was more representative of the real situation in vivo.

In the present experimental study, the pharmacological treatment was carried out according to two methods of administration:

a) one drop (10 μL) was instilled directly on the surface of the right eye cornea of the rabbit with a micropipette. In the left eye, using the same method, the vehicle alone was instilled (corresponding reference solution).

b) 6 instillations (10 μL) over a period of 18-20 minutes directly on the right corneal surface. In the left eye, using the same method, the vehicle alone was instilled (corresponding reference solution).

4, while for iris was between 0 and 2. The ocular irritation index alone does not allow an assessment of the eye irritancy power.

The overall evaluation was performed following the FDA recommendations, according to which a substance is considered to be an eye irritant if at least four animals out of six show any positive reaction in at least one of the three areas taken into consideration. A substance causing any lesions to the cornea or iris, which do not heal within seven days, is classified as highly irritating.

TABLE 2

Scale of scores for the assessment of corneal irritation

| Location of the lesion | Type of lesion | Assigned Score |
|---|---|---|
| Corneal Opacity | No ulceration or opacity | 0 |
| Corneal Opacity | Distinct or confluent areas of opacity (other than slight dulling of normal luster); details of iris clearly visible | 1 |
| Corneal Opacity | Easily discernible translucent area; details of iris slightly obscured | 2 |
| Corneal Opacity | Opalescent areas; no details of iris visible and size of pupil barely discernible | 3 |
| Corneal Opacity | Completely opaque cornea; iris not discernible through the opacity | 4 |
| Iris | Normal | 0 |
| Iris | Rugae markedly deepened than normal; congestion, swelling, moderate circumcorneal injection; reaction to light preserved | 1 |
| Iris | No reaction to light, hemorrhage; gross destruction | 2 |
| Conjunctival redness (bulbar and palpebral conjunctivae) | Normal blood vessels | 0 |
| Conjunctival redness (bulbar and palpebral conjunctivae) | Blood vessels slightly injected; hyperemia | 1 |
| Conjunctival redness (bulbar and palpebral conjunctivae) | Diffuse, crimson color; individual injected vessels not easily discernible | 2 |
| Conjunctival redness (bulbar and palpebral conjunctivae) | Diffuse beefy red | 3 |

Treatment Evaluation

The eyes of the rabbits were examined at the end of each treatment (time 0), and in the following hours (1 and 3 hours after exposure), and the following day (24 hours after the treatment).

In the order, the following were examined: conjunctiva, iris and cornea.

Cornea and iris lesions were detected by direct observation and by illumination by means of an ultraviolet lamp, following instillation of an isotonic aqueous solution of fluorescein.

The severity of lesions was expressed by scores according to the grading scale shown in Table 2.

The scores assigned to the various observations were processed according to a recent amendment of the original method from Draize (Wilhelmus, 2001). The scores obtained for the different ocular areas analyzed (conjunctiva, iris, and cornea), for each animal at a given timepoint, were summed together to obtain the overall irritation index. Unlike what had been proposed by Draize in the original method, the score obtained for the single variables was not multiplied by a correction factor, but each variable was assigned with a score comprised in different ranges. For example, the range of scores for corneal opacity was comprised between 0 and Total score equals to the sum of the all scores assigned to cornea, iris and conjunctiva.

Results

No animals died during the course of treatments (a and b), and no ocular effects were observed at the time of instillation of the solutions (blinking, closed eyelids, watery eyes). In addition, no clinical alteration or changes were observed in any of the treated animals. The ocular reaction results are reported in Tables 3-5 for treatment a), and 6-8 for treatment b).

From the results obtained, it can be concluded that the formulations are not irritant and they are biocompatible after both treatments.

TABLE 3

Treatment a) with Solution 1

| Time | Solution 1 | | Ref 1 | |
|---|---|---|---|---|
| (hours) | Individual scores | Mean | Individual scores | Mean |
| 0 | 0 0 0 | 0 | 0 0 0 | 0 |
| 1 | 0 0 0 | 0 | 0 0 0 | 0 |

TABLE 3-continued

Treatment a) with Solution 1

| Time (hours) | Solution 1 Individual scores | | | Mean | Ref 1 Individual scores | | | Mean |
|---|---|---|---|---|---|---|---|---|
| 3 | 0 | 0 | 0 | 0 | 0 | 0 | 0 | 0 |
| 24 | 0 | 0 | 0 | 0 | 0 | 0 | 0 | 0 |

TABLE 4

Treatment a) with Solution 2

| Time (hours) | Solution 2 Individual scores | | | Mean | Ref 2 Individual scores | | | Mean |
|---|---|---|---|---|---|---|---|---|
| 0 | 0 | 0 | 0 | 0 | 0 | 0 | 0 | 0 |
| 1 | 0 | 0 | 0 | 0 | 0 | 0 | 0 | 0 |
| 3 | 0 | 0 | 0 | 0 | 0 | 0 | 0 | 0 |
| 24 | 0 | 0 | 0 | 0 | 0 | 0 | 0 | 0 |

TABLE 5

Treatment a) with Solution 3

| Time (hours) | Solution 3 Individual scores | | | Mean | Ref 3 Individual scores | | | Mean |
|---|---|---|---|---|---|---|---|---|
| 0 | 0 | 0 | 0 | 0 | 0 | 0 | 0 | 0 |
| 1 | 0 | 0 | 0 | 0 | 0 | 0 | 0 | 0 |
| 3 | 0 | 0 | 0 | 0 | 0 | 0 | 0 | 0 |
| 24 | 0 | 0 | 0 | 0 | 0 | 0 | 0 | 0 |

TABLE 6

Treatment b) with Solution 1

| Time (hours) | Solution 1 Individual scores | | | Mean | Ref 1 Individual scores | | | Mean |
|---|---|---|---|---|---|---|---|---|
| 0 | 0 | 0 | 0 | 0 | 0 | 0 | 0 | 0 |
| 1 | 0 | 0 | 0 | 0 | 0 | 0 | 0 | 0 |
| 3 | 0 | 0 | 0 | 0 | 0 | 0 | 0 | 0 |
| 24 | 0 | 0 | 0 | 0 | 0 | 0 | 0 | 0 |

TABLE 7

Treatment b) with Solution 2

| Time (hours) | Solution 2 Individual scores | | | Mean | Ref 2 Individual scores | | | Mean |
|---|---|---|---|---|---|---|---|---|
| 0 | 0 | 0 | 0 | 0 | 0 | 0 | 0 | 0 |
| 1 | 0 | 0 | 0 | 0 | 0 | 0 | 0 | 0 |
| 3 | 0 | 0 | 0 | 0 | 0 | 0 | 0 | 0 |
| 24 | 0 | 0 | 0 | 0 | 0 | 0 | 0 | 0 |

TABLE 8

Treatment b) with Solution 3

| Time (hours) | Solution 3 Individual scores | | | Mean | Ref 3 Individual scores | | | Mean |
|---|---|---|---|---|---|---|---|---|
| 0 | 0 | 0 | 0 | 0 | 0 | 0 | 0 | 0 |
| 1 | 0 | 0 | 0 | 0 | 0 | 0 | 0 | 0 |
| 3 | 0 | 0 | 0 | 0 | 0 | 0 | 0 | 0 |
| 24 | 0 | 0 | 0 | 0 | 0 | 0 | 0 | 0 |

Example 10

Evaluation of PCA Ex Vivo Transcorneal Permeation of a Composition According to Example 2 Through Isolated Rabbit Cornea.

Topical administration is the desired route for the administration of ophthalmic drugs acting on the periocular area and/or anterior segment.

The cornea is the main barrier to the absorption of drugs (Ghate and Edelhauser, 2008; J Glaucoma, 17:147-156), and it is a structure consisting of several layers: epithelium, stroma, and endothelium. The diffusion through the corneal epithelium is considered the rate determining step in the transcorneal permeation of most drugs. Therefore, the ability of a compound to cross the cornea is the dominant process, and it is based mainly on the balance between the hydrophilic and lipophilic properties of the compound. In addition to serving as a diffusion barrier to limit drug penetration, the cornea expresses certain enzymes that metabolize drugs, and active transport systems that might participate in drug metabolism (esterase) (Shirasaki, 2008; J Pharmaceutical Sciences, 97:2462-2496).

Ex Vivo Corneal Permeability Study

For the determination of ex vivo corneal permeability, rabbit corneas obtained after proptosis of the eye, performed immediately after the animal euthanization, were used. The rabbits were New Zealand albino rabbits (n=3) and were euthanized by intravenous injection of Pentothal sodium (Farmaceutici Gellini, Aprilia, Italy). After the eyes were proptosed, the cornea, with 2 mm of sclera, was immediately excised and mounted in a perfusion apparatus. During the preparation, particular attention was paid to prevent the exfoliation of the corneal epithelium and its contact with any solid surfaces.

The perfusion apparatus used for the determination of PCA corneal permeability was entirely in plexiglas, and consisted of a donor chamber (epithelial side, 1.0 mL volume) and a receiving compartment (endothelial side, volume equals to 5.0 mL) in order to ensure sink conditions (Saettone et al., 1996; Int. J Pharmaceutics, 142:103-113). The two compartments were separated by the interposition of the isolated cornea, and the apparatus was thermostat maintained at 32° C. by contact with a heated plate. The cornea was kept in place with the physiological curvature as a result of the pressure difference caused by the solution column on the endothelial side, without any mechanical constraints which could cause damage to the cellular structures. During the permeation study, the area of the corneal surface in contact with the donor solution was 1.52 cm$^2$.

The donor solution was comprised of a Ringer-Bicarbonate Buffer (RBB) solution at pH=7.6 and osmolality of 290-295 mOsmol/Kg. The composition of the buffer was the following: sodium chloride 6.200 g/L, potassium chloride 0.358 g/L, potassium dihydrogen phosphate dihydrate 0.103 g/L, sodium bicarbonate 2.454 g/L, calcium chloride dihydrate 0.115 g/L, magnesium chloride hexahydrate 0.159 g/L, and glucose 0.900 g/L in purified water (Milli-Q) added with 0.02% w/w of PCA and 0.04% w/w of hyaluronic acid (HA).

The amounts of PCA and HA were five times lower than those present in the experimental solution n. 2 (Solution 2 of Example 2), but the same PCA vs HA percentage ratio was maintained. The RBB solution itself was the receiving phase.

To ensure oxigenation, essential to preserve the cornea viability and agitation of the solutions, an $O_2/CO_2$ (95:5) mixture was bubbled through each compartment at a flow rate of about 3-4 bubbles/s. Before starting the permeation experiment, the cornea was equilibrated by keeping it in contact with the RBB solution, both on the endothelial and epithelial side, for 10 min; then the solution placed on the epithelial side was withdrawn and replaced with 1.0 mL of a fresh RBB solution containing the established amount of PCA. The amount of PCA added to the donor phase allowed to have sufficient concentration gradient to favor the diffusion of the drug from the donor to the receiving compartment, and was comparable to the dilution reported for similar studies in the literature data.

After the permeation experiment start, at appropriate intervals of time (15, 30, 60, 90, 120, 180 and 240 minutes), 0.50 mL of solution were withdrawn from the receiving compartment (endothelial side) and replaced with fresh RBB. At the end of the experiment, the entire donor phase was collected and submitted to quantitative determination of the active ingredient in a similar manner as provided for the samples of the receiving phase.

Quantitative analysis of PCA was performed by HPLC using a C18 reverse phase column C18 (Bondclone 10 μm 300×3.9 mm), and the eluent was a 98:2 mixture buffer solution to acetonitrile. The buffer solution was comprised of 4.3 mM HCl and 0.1 mM sodium hexanesulfonate. The analysis of the sample was performed at A=210 nm, and the retention time was 2.89 min under the experimental conditions. For standard PCA concentrations, comprised between 0.0996 and 10,0601 μg/mL, the linear correlation ($R^2$) between the experimental points resulted to be 0.9992.

Results

In FIG. 1 the permeation profile of pyrrolidone carboxylic acid (PCA) through isolated rabbit cornea may be observed.

The obtained results demonstrate PCA tendency to permeate through isolated rabbit cornea under the experimental conditions; in fact, a small percentage of PCA permeated to the receiving compartment where it was found, at the end of the experiment, the 0.051% w/w of the amount present in the donor compartment. The results allow to calculate a PCA corneal permeability of $0.395 \cdot 10^{-5}$ cm/s.

PCA is a highly hydrophilic molecule with a partition coefficient octanol/water (PO/W) of 0.069, and uses the paracellular pathway to permeate the epithelial barrier, which is the main barrier to corneal permeation, according to what reported in the literature for sodium fluorescein, which is often used as the model drug for hydrophilic drugs. However, the PO/W value for sodium fluorescein is 2.18, i.e. less hydrophilic than PCA, with a permeability through porcine cornea of $0.05 \cdot 10^{-5}$ cm/s (Pescina et al, 2015; J Pharmaceutical Sciences, 104:63-71). Presumably, fluorescein will have a greater affinity for the epithelium compared to PCA.

It is known in the literature that the permeability of drugs through bovine and porcine cornea is usually from three to nine times lower than the one referred to the rabbit cornea; it is therefore surprising that PCA, markedly more hydrophilic, is able to permeate through the rabbit cornea with permeability almost equal to that of fluorescein. In conclusion, despite the presence of the corneal epithelial barrier effect against PCA, its transdermal permeation ability, despite poor, demonstrates the drug affinity for the cornea, and its ability to be only partly affected by the corneal epithelial barrier effect. Furthermore, although poor, PCA ability to cross the cornea denotes a certain affinity of the drug for this tissue and presuppose a possible uptake by the strongly hydrophilic corneal stroma, which could act as a depot for this molecule. The drug may therefore not cross the corneal barrier quantitatively, but it remains in contact with the tissue for extended times.

The invention claimed is:

1. A method for treating ocular diseases and/or disorders in a subject, comprising administering to a subject (i) pyrrolidone carboxylic acid and/or a pharmaceutically acceptable salt thereof, wherein the pharmaceutically acceptable salt is selected from the group consisting of: carbonate, hydrochloride, hydrobromide, sulfate, hydrogen sulfate, citrate, maleate, fumarate, trifluoroacetate, 2-naphthalenesulfonate, and para-toluenesulfonate, and (ii) one or more active ingredient selected from the group consisting of a metal salt, hyaluronic acid, a cellulose derivative, an osmoprotectant, and a mixture thereof, wherein (i) and (ii) are the only active ingredients administered to the subject.

2. The method according to claim 1, wherein said one or more active ingredient of (ii) is a metal salt of a copper, zinc, sodium, manganese salt, or a mixture thereof.

3. The method according to claim 1, wherein said one or more active ingredient of (ii) is a cellulose derivative of carboxymethyl cellulose, ethyl cellulose, hydroxypropyl cellulose, or a mixture thereof.

4. The method according to claim 1, wherein said one or more active ingredient of (ii) is an osmoprotectant of erythritol, taurine, L-carnitine, or a mixture thereof.

5. The method according to claim 1, wherein said ocular diseases and/or disorders are selected from the group consisting of: ocular dryness, ocular hyperosmolarity, ocular inflammations, ocular infections, and blepharitis.

6. The method according to claim 5, wherein said ocular inflammations or ocular infections are due to bacteria and/or viruses.

7. The method according to claim 1, wherein said pyrrolidone carboxylic acid and/or pharmaceutically acceptable salts thereof is administered in a pharmaceutical formulation having a pH between 6 and 7.5.

8. The method according to claim 7, wherein the pharmaceutical formulation has a pH between 6.6 and 7.

9. The method according to claim 1, wherein said pyrrolidone carboxylic acid and/or pharmaceutically acceptable salts thereof is administered in an amount from 0.05% to 1% by weight.

10. The method according to claim 9, wherein said pyrrolidone carboxylic acid and/or pharmaceutically acceptable salts thereof is administered in an amount of 0.1 to 0.2% by weight.

* * * * *